(12) United States Patent
Canalini

(10) Patent No.: US 7,404,947 B2
(45) Date of Patent: Jul. 29, 2008

(54) HAIR TREATMENT LOTION

(76) Inventor: Maria Grazia Canalini, Piazza Dante, 23, 41024 Le Piane Di Lama Mocogno (IT)

( * ) Notice: Subject to any disclaimer, the term of this patent is extended or adjusted under 35 U.S.C. 154(b) by 0 days.

(21) Appl. No.: 10/536,497

(22) PCT Filed: Dec. 12, 2003

(86) PCT No.: PCT/EP03/14124

§ 371 (c)(1), (2), (4) Date: May 25, 2005

(87) PCT Pub. No.: WO2004/056328

PCT Pub. Date: Jul. 8, 2004

(65) Prior Publication Data

US 2006/0134058 A1 Jun. 22, 2006

(30) Foreign Application Priority Data

Dec. 19, 2002 (IT) .......................... MO2002A0363

(51) Int. Cl.
- *A01N 65/00* (2006.01)
- *A61K 8/97* (2006.01)
- *A61K 36/82* (2006.01)
- *A61Q 5/00* (2006.01)

(52) U.S. Cl. ................ 424/70.1; 424/74; 424/729; 424/773; 424/774

(58) Field of Classification Search ................ 424/401, 424/70.1, 74, 725, 729, 773, 774
See application file for complete search history.

(56) References Cited

U.S. PATENT DOCUMENTS 5,053,222 A * 10/1991 Takasu et al. ............... 514/106

FOREIGN PATENT DOCUMENTS

JP  08048616  *  2/1996
JP  11139943  *  5/1999

OTHER PUBLICATIONS

Patent Abstracts of Japan—& JP 11 139943 A (Yokohama Tsunetaka; Handa Kayoko), May 25, 1999 abstract.
Database WPI—Derwent Publications Ltd., London, GB; AN 1994-124075—XP002276617 "Tonic agent preventing baldness-contains extract of Cucurbitaceae, Phellodendron, Gentianaceae, etc. plants" & JP 06 072828 A (Hatano T.), Mar. 15, 1994 abstract.
Database WPI—Derwent Publications Ltd., London, GB; AN 2001-571151—XP002276618 "Ginkgo health-care tea." & CN 1 303 606 A (Liu L.), Jul. 18, 2001 abstract.

* cited by examiner

*Primary Examiner*—Johann R. Richter
*Assistant Examiner*—Konata M George
(74) *Attorney, Agent, or Firm*—Hoffman, Wasson & Gitler, PC

(57) ABSTRACT

The invention provides a hair treatment lotion of green tea, gentian, and geranium in aqueous solution, and methods for using this lotion to prevent or treat hair loss.

14 Claims, No Drawings

HAIR TREATMENT LOTION

TECHNICAL FIELD

The present invention relates to a hair treatment lotion.

BACKGROUND ART

It is known that in recent years the problem of baldness, i.e., gradual hair loss, has become very important and a highly topical issue, since it affects many people, both men and women.

Baldness can in fact cause considerable discomfort in the people that it affects, both on an aesthetic level and sometimes on a psychological level.

As a consequence of the diffusion of this phenomenon, various medical, surgical and/or cosmetological therapies have been developed and proposed in an attempt to limit and slow hair loss.

Some treatments, for example, propose medical and/or cosmetological therapies of various kinds depending on the extent of the loss and thinning: these therapies allow to achieve an initial stabilization of hair loss a few months after the beginning of the treatment.

Many lotions having different compositions and different methods of application are in fact currently commercially available.

These lotions are usually recommended for stopping hair loss and/or facilitate hair regrowth.

However, these therapies do not allow to achieve a permanent result, since when the treatment is suspended the phenomenon reappears in a form that is generally more acute and can be contained only by resorting to surgical procedures.

Moreover, some of these lotions can cause several side effects in case of particular sensitivity to the substances they contain and can have contraindications for use by individuals who have certain disorders, such as hypertension, migraines or vascular problems in general.

Intolerance to the substances contained in known lotions has caused for example transient itching localized to the scalp or diffused over the entire body, skin inflammations caused by irritations or eczemas of an allergic nature: more rarely there have been cases of headache, vertigo or hypertrichosis.

In all these cases it is generally necessary to suspend the treatments immediately and therefore any benefits achieved are lost.

As an alternative, particularly for individuals with full-blown baldness, surgical procedures are proposed which can be performed according to several methods and in general consist in repositioning healthy hair in bald areas, removing and reimplanting scalp portions so as to restore a harmonious and aesthetically pleasant hair distribution.

These procedures are generally performed under local anesthetic and can be more or less invasive depending on the method used.

However, these known procedures are not free from drawbacks, including the fact that they do not ensure permanent and durable results, since rather often the implants of synthetic hair are rejected within 6-12 months of the procedures, and a new surgical procedure therefore becomes necessary to remove the rejected hair.

Further, these procedures cannot be performed on all individuals affected by baldness.

In order to reduce the risk of postoperative complications, such as infections or the like, it is in fact necessary to perform preventive medical therapies that use for example lotions based on cortisone or antibiotic substances, which cannot be used by certain individuals who have particular allergies or specific disorders.

DISCLOSURE OF THE INVENTION

The aim of the present invention is to eliminate the drawbacks noted above of known treatments and procedures, by devising a hair treatment lotion that allows to solve permanently the problem of baldness and to promote hair regrowth and can be used by all individuals affected by hair loss, without any restriction of use due for example to contraindications of use or side effects.

Within this aim, an object of the present invention is to allow easy and practical application on the part of the affected individuals.

In view of this aim and this and other objects that will become better apparent hereinafter, according to the present invention a hair treatment lotion is provided which is characterized in that it comprises green tea, gentian and geranium mixed with at least one solution medium.

The solution medium can be constituted by an aqueous base, a physiological solution, or the like.

The aqueous base can be constituted preferably by distilled water ($H_2O$).

The green tea is used in leaf form; the gentian is used in the form of dried and chopped root; the geranium is used as essence.

The green tea, gentian and geranium essence are preferably present in the following mutually independent quantities for every 1500 ml of $H_2O$:

green tea, 0.1 to 0.5 g; gentian, 0.001 g to 0.3 g; geranium essence, 20 to 50 drops.

Each one of the geranium essence drops has a weight comprised between 0.01 g and 0.07 g.

Conveniently, by mixing said components the lotion is ready for use.

As is known, each hair is composed of a so-called shaft, which protrudes partially from the scalp, and of a root or bulb, which is inserted obliquely in the scalp.

The root is formed by a recess in which the vessels and nerves that constitute the papilla are arranged.

The fibers that constitute hair form through a process of keratinization of the epithelial cells that are in contact with the papilla (matrix).

Hair is in fact constituted by a keratin shaft formed by fibers and fibrils formed by chains of amino acids coiled in a spiral and bonded by sulfur bridges.

In normal conditions, the sebum produced by the sebaceous glands that are present in the scalp drips along the hair, constituting a natural protection against external agents.

In cases of hyperseborrhea, i.e., of excessive sebum production, there are negative effects on hair health; the excess of sebum in fact over time obstructs the insertion point of the hair in the scalp, choking the cells that constitute the hidden part of the shaft, the root and the sebaceous gland associated with the hair.

In these cases, the metabolic activity of the cells is seriously compromised and hair weakens until it falls; as a consequence of these phenomena, the cells of the matrix are no longer capable of generating a new hair.

Conveniently, it has been found that the lotion according to the invention allows to restore conditions that are suitable for the growth of new hair; the green tea, gentian and geranium act synergistically, mutually enhancing their respective properties.

Green tea is in fact used to remove the grease that obstructs the pores of the scalp from which hair protrudes; gentian, rich in stimulating active ingredients, acts on the sebaceous glands, stimulating resumption of normal activity; finally, geranium has active ingredients that affect the cells of the matrices in order to stimulate the growth of new hair.

The lotion according to the invention is applied advantageously in hair loss treatments, such as hair loss prevention treatments and/or treatments for facilitating the growth of new hair.

The lotion can be used to treat baldness of any degree and extent and has no contraindication of use or any side effect.

The treatment consists in performing, for a first period, one daily application of the lotion, massaging the portion of scalp being affected.

Subsequently, it is sufficient to perform a maintenance treatment, which provides for one weekly application of the lotion for a few additional months.

The time required for growth of new hair is linked to the time elapsed since the "death" of the bulb, and therefore the first hair to appear is the hair lost most recently and the last hair is the hair that fell longest ago.

The first results are apparent 2-3 months after starting the treatment; fine hairs appear initially, becoming stronger over time and producing the final hair.

The following examples are given only by way of illustration of the present invention and must not be understood as limiting the scope of the present invention as defined by the appended claims.

EXAMPLE 1

A first hair treatment lotion that can be obtained from a mixture of the following substances:

| | |
|---|---|
| Green tea | 0.15 g |
| Gentian | 0.10 g |
| Geranium essence | 30 drops |
| $H_2O$ | 1500 ml |

EXAMPLE 2

A second hair treatment lotion that can be obtained from a mixture of the following substances:

| | |
|---|---|
| Green tea | 0.20 g |
| Gentian | 0.12 g |
| Geranium essence | 36 drops |
| $H_2O$ | 1500 ml |

EXAMPLE 3

A third hair treatment lotion that can be obtained from a mixture of the following substances:

| | |
|---|---|
| Green tea | 0.30 g |
| Gentian | 0.15 g |
| Geranium essence | 40 drops |
| $H_2O$ | 1500 ml |

The disclosures in Italian Patent Application No. MO2002A000393 from which this application claims priority are incorporated herein by reference.

What is claimed is:

1. A hair treatment lotion consisting of green tea, gentian, and geranium mixed with at least one solution medium, wherein the solution medium is an aqueous base or a physiological solution.

2. The lotion of claim 1, wherein said aqueous base is distilled water.

3. The lotion of claim 1, wherein said green tea is in leaf form.

4. The lotion of claim 3, wherein said green tea leaves are dried.

5. The lotion of claim 1, wherein said gentian is in root form.

6. The lotion of claim 5, wherein said gentian root is dried and chopped.

7. The lotion of claim 1, wherein said geranium is in essence form.

8. The lotion of claim 1, wherein said green tea is present in an amount between about 0.1 g and 0.5 g for every 1500 ml of said solution medium.

9. The lotion of claim 1, wherein said gentian is present in an amount between about 0.001 g and 0.3 g for every 1500 ml of said solution medium.

10. The lotion of claim 1, wherein said geranium is present in an amount between about 20 and 50 drops for every 1500 ml of said solution medium.

11. The lotion of claim 2, wherein said green tea, said gentian, said geranium and said water are present in the following quantities:

| | |
|---|---|
| Green tea | 0.20 g |
| Gentian | 0.12 g |
| Geranium essence | 36 drops |
| $H_2O$ | 1500 ml. |

12. The lotion of claim 11, wherein each one of said drops has a weight between about 0.01 g and 0.07 g.

13. A method for preventing hair loss comprising applying the lotion of claim 1 to an afflicted scalp in an amount and frequency sufficient to prevent hair loss.

14. A method for promoting the growth of new hair comprising applying the lotion of claim 1 to an afflicted scalp in an amount and frequency sufficient to restore conditions suitable for the growth of new hair.

* * * * *